United States Patent
Kajita et al.

(10) Patent No.: US 10,401,329 B2
(45) Date of Patent: Sep. 3, 2019

(54) ROTATING MACHINE ABNORMALITY DETECTION DEVICE, METHOD AND SYSTEM, AND ROTATING MACHINE

(71) Applicant: Kobe Steel, Ltd., Hyogo (JP)

(72) Inventors: Masakazu Kajita, Kobe (JP); Eiji Takahashi, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 261 days.

(21) Appl. No.: 15/327,895

(22) PCT Filed: Aug. 18, 2015

(86) PCT No.: PCT/JP2015/073118
§ 371 (c)(1),
(2) Date: Jan. 20, 2017

(87) PCT Pub. No.: WO2016/039087
PCT Pub. Date: Mar. 17, 2016

(65) Prior Publication Data
US 2017/0212085 A1 Jul. 27, 2017

(30) Foreign Application Priority Data
Sep. 12, 2014 (JP) ................. 2014-185872

(51) Int. Cl.
*G01N 29/44* (2006.01)
*G01M 99/00* (2011.01)
(Continued)

(52) U.S. Cl.
CPC ........ *G01N 29/4445* (2013.01); *G01M 13/00* (2013.01); *G01M 13/045* (2013.01);
(Continued)

(58) Field of Classification Search
CPC .... G01N 29/4445; G01N 29/12; G01N 29/46; G01R 23/16; G01M 13/00; G01M 13/045; G01M 99/00
See application file for complete search history.

(56) References Cited

U.S. PATENT DOCUMENTS

| | | | | |
|---|---|---|---|---|
| 4,453,407 A | * | 6/1984 | Sato | ........... G01H 1/003 702/56 |
| 6,904,371 B2 | * | 6/2005 | Sonnichsen | ...... G01M 13/028 702/190 |

(Continued)

FOREIGN PATENT DOCUMENTS

| | | |
|---|---|---|
| CN | 1490527 A | 4/2004 |
| CN | 201637483 U | 11/2010 |

(Continued)

OTHER PUBLICATIONS

Extended European Search Report issued by the European Patent Office on Apr. 9, 2018, which corresponds to EP15839251.4—1001 and is related to U.S. Appl. No. 15/327,895.

(Continued)

*Primary Examiner* — Justin Seo
*Assistant Examiner* — John M Royston
(74) *Attorney, Agent, or Firm* — Studebaker & Brackett PC (57) ABSTRACT

An abnormality detection device, an abnormality detection method and an abnormality detection system for a rotating machine according to the present invention sample a vibration of a rotating machine at a predetermined sampling frequency, output for each predetermined period of time a set of a plurality of samples detected within the predetermined period of time, store the set of samples in a storage section, perform frequency analysis on the set of samples, and display in real time frequency analysis results in chronological order. A rotating machine according to the present invention includes the abnormality detection device.

10 Claims, 4 Drawing Sheets

(51) Int. Cl.
*G01N 29/12* (2006.01)
*G01N 29/46* (2006.01)
*G01M 13/00* (2019.01)
*G01M 13/045* (2019.01)
*G01R 31/34* (2006.01)

(52) U.S. Cl.
CPC ............ *G01M 99/00* (2013.01); *G01N 29/12* (2013.01); *G01N 29/46* (2013.01); *G01R 31/343* (2013.01)

(56) References Cited

U.S. PATENT DOCUMENTS

| 2004/0064277 | A1  | 4/2004 | Samata et al. |
| 2014/0230555 | A1* | 8/2014 | Cerny ............... F01D 11/20 73/593 |

FOREIGN PATENT DOCUMENTS

| JP | S60-086429 A  | 5/1985  |
| JP | H08-166330 A  | 6/1996  |
| JP | 2002-181038 A | 6/2002  |
| JP | 2010-234403 A | 10/2010 |

OTHER PUBLICATIONS

Revision: "Operating Manual and Programming Reference Model SR785 Dynamic Signal Analyzer", Stanford Research Systems, Inc. All Rights Reserved, vol. 1, Dec. 1, 2006, 546 pages.

Notification of Transmittal of Translation of the International Preliminary Report on Patentability (Chapter I) and Translation of Written Opinion of the International Searching Authority; PCT/JP20151073118; dated Mar. 23, 2017.

International Search Report issued in PCT/JP2015/073118; dated Nov. 10, 2015.

\* cited by examiner

ROTATING MACHINE ABNORMALITY DETECTION DEVICE, METHOD AND SYSTEM, AND ROTATING MACHINE

TECHNICAL FIELD

The present invention relates to an abnormality detection device, an abnormality detection method, and an abnormality detection system for a rotating machine for suitably detecting an abnormality in a rotating machine such as a rotor abnormality. In addition, the present invention relates to a rotating machine including the abnormality detection device for a rotating machine.

BACKGROUND ART

In rotating machines such as a turbine and a compressor, a rotor usually rotates at a high speed in an operating state. Therefore, when an abnormality such as damage occurs in the rotor, for example, the abnormality such as damage increases as detection of the abnormality is delayed, so that the rotating machine may stop due to the abnormality. Accordingly, such an abnormality in a rotating machine is desired to be detected and notified promptly.

For example, an abnormal sliding diagnostic device disclosed in Patent Literature 1 uses an AE (Acoustic Emission) sensor to detect an AE signal from a rotating machine and performs frequency analysis on the detected AE signal to thereby determine the presence/absence and, if any, the position and the degree of an abnormal sliding and display a determination result.

If the chronological change in the operating state of a rotating machine can be recognized, an operator can find a chronological change in the operating state of the rotating machine, which makes it possible to detect an abnormality in the rotating machine more promptly. However, in the conventional technique disclosed in Patent Literature 1, although a determination result about the presence/absence, the position, and the degree of an abnormal sliding is displayed, the chronological change in determination results is not displayed. Therefore, although the conventional technique allows recognition of the presence/absence and the like of an abnormality in a rotating machine, it has been difficult to promptly detect the abnormality.

CITATION LIST

Patent Literature

Patent Literature 1: Japanese Unexamined Patent Publication No. HEI 8-166330

SUMMARY OF INVENTION

The present invention has been made in view of the above-mentioned problem, and has an object of providing an abnormality detection device, an abnormality detection method, and an abnormality detection system for a rotating machine which are capable of promptly detecting an abnormality in a rotating machine. In addition, the present invention provides a rotating machine including the abnormality detection device for a rotating machine.

An abnormality detection device, an abnormality detection method and an abnormality detection system for a rotating machine according to the present invention sample a vibration of a rotating machine at a predetermined sampling frequency, output for each predetermined period of time a set of a plurality of samples detected within the predetermined period of time, store the set of samples in a storage section, perform frequency analysis on the set of samples, and display in real time frequency analysis results in chronological order. Therefore, the abnormality detection device, the abnormality detection method, and the abnormality detection system for a rotating machine according to the present invention can promptly detect an abnormality in a rotating machine. A rotating machine according to the present invention includes such abnormality detection device. Therefore, according to the present invention, a rotating machine including the above-mentioned abnormality detection device for a rotating machine is provided.

These and other objects, features and advantages of the present invention will become more apparent upon reading the following detailed description along with the accompanying drawings.

DESCRIPTION OF EMBODIMENTS

Hereinafter, an embodiment of the present invention will be described with reference to the accompanying drawings. Elements denoted by the same reference numerals in the drawings have the same configuration and therefore, a repeated description will be appropriately omitted. In the present specification, those elements having the same configuration are denoted by the same reference numeral when being referred to collectively, and are denoted by the same reference numeral accompanied by a different respective reference character when being referred to individually.

Figure 1:
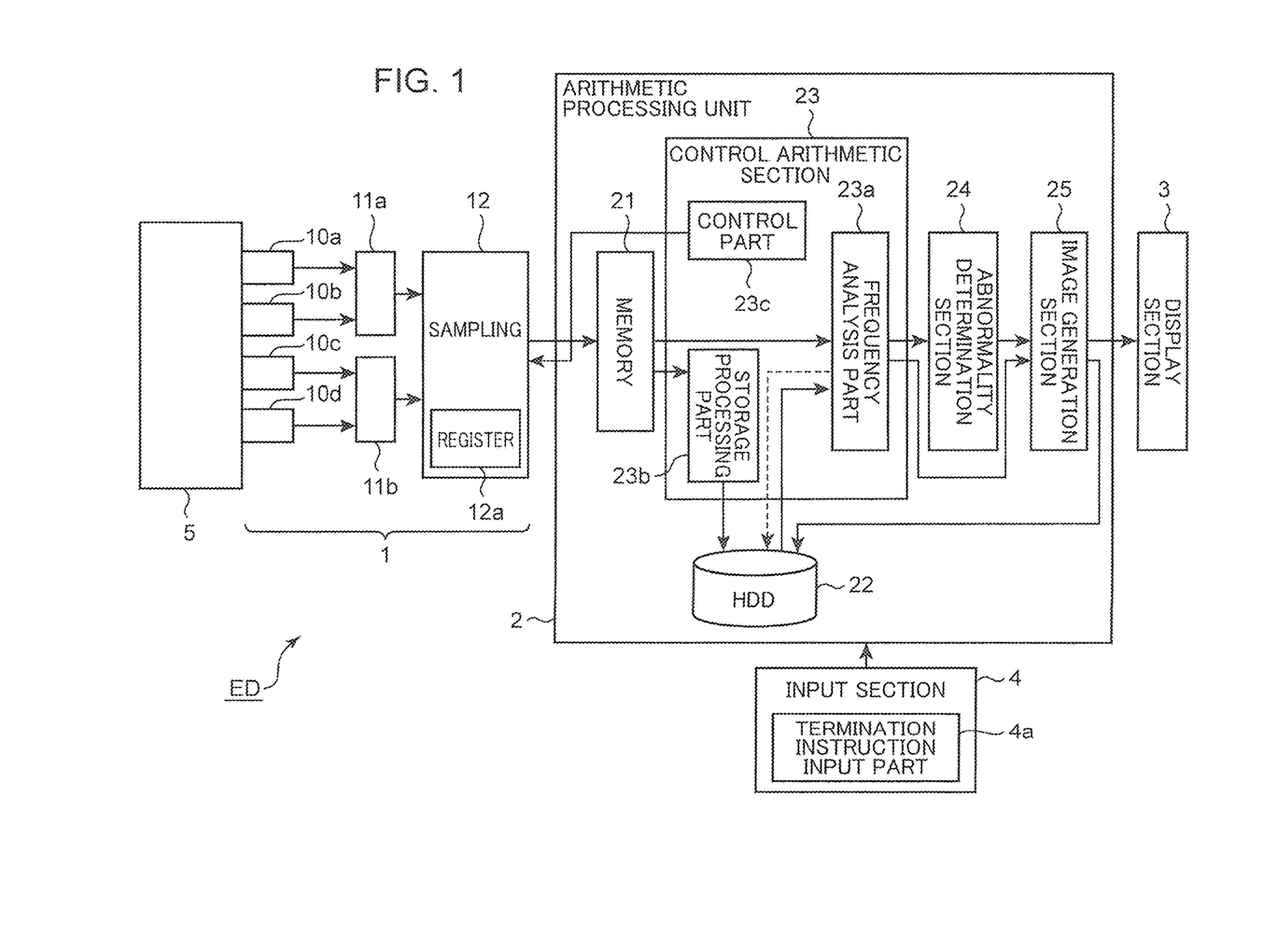
FIG. 1 is a block diagram showing an example of a configuration of an abnormality detection device for a rotating machine according to an embodiment.

FIG. 1 is a block diagram showing an example of a configuration of an abnormality detection device for a rotating machine (hereinafter, also referred to merely as "abnormality detection device") ED according to an embodiment. As shown in FIG. 1, the abnormality detection device ED includes, for example, a detection unit 1, an arithmetic processing section 2, a display section 3, and an input section 4. The detection unit 1 and the arithmetic processing section 2 are connected to each other, and the arithmetic processing section 2 and the display section 3 are connected to each other. The input section 4 is connected to the arithmetic processing section 2.

The detection unit 1 is a device for sampling a vibration of a rotating machine 5 to be measured at a predetermined sampling frequency, and outputting, for each predetermined period of time, a set of a plurality of samples detected within the predetermined period of time. The detection unit 1 includes, for example, sensors 10 (10a to 10d), amplifiers 11 (11a and 11b), and a sampling part 12. The sensors 10 and the amplifiers 11 are connected to each other, the amplifiers 11 and the sampling part 12 are connected to each other, and the sampling part 12 and the arithmetic processing section 2 are connected to each other.

The sensors 10 are devices for detecting a vibration of the rotating machine 5 to be measured. The sensors 10 are, for example, in the form of electromechanical sensing elements which include material such as piezoelectric ceramics to convert mechanical energy of a vibration into electrical energy. More specifically, the sensors 10 include, for example, an AE (Acoustic Emission) sensor and an accelerometer. One or a plurality of sensors 10 may be used and, in the present embodiment, the sensors 10 include two AE sensors 10a, 10b and two accelerometers 10c, 10d. The AE sensors 10a, 10b and the accelerometers 10c, 10d are, as shown in FIG. 1, attached to the body of the rotating machine 5 in the form of a turbine, a compressor, or the like. For example, when the rotating machine 5 is in the form of a compressor, and a rotor abnormality, such as a contact between two rotors usually spaced from each other, occurs, the AE sensors 10a, 10b detect an AE wave due to the abnormality. The accelerometers 10c, 10d detect the abnormality based on an acceleration of a vibration of the rotating machine 5.

The amplifiers 11 are devices for amplifying each minute detection signal outputted from the sensors 10. An appropriate number of amplifiers 11 may be used according to the number of sensors 10 and, in the present embodiment, the amplifiers 11 include two amplifiers 11a, 11b. The amplifier 11a is connected to the AE sensors 10a, 10b. The amplifier 11b is connected to the accelerometers 10c, 10d. The amplifier 11a individually amplifies and outputs signals outputted from the AE sensors 10a, 10b. The amplifier 11b individually amplifies and outputs signals outputted from the accelerometers 10c, 10d. The amplifiers 11a, 11b supply the respective outputs to the sampling part 12.

The sampling part 12 is a device for sampling a vibration of the rotating machine 5 at a predetermined sampling frequency, and outputting a set of a plurality of samples to the arithmetic processing section 2. The sampling part 12 outputs the set of samples in accordance with an instruction from the arithmetic processing section 2. In the present embodiment, for example, the sampling part 12 includes a register 12a, and samples respective signals of the AE sensors 10a, 10b individually outputted from the amplifier 11a at a sampling frequency of 1 MHz at the same timing and individually, and performs analog-to-digital conversion of the sampled signals and accumulates them in the register 12a. On the other hand, the sampling part 12 samples respective signals of the accelerometers 10c, 10d individually outputted from the amplifier 11b at a sampling frequency of 20 kHz at the same timing and individually, and performs analog-to-digital conversion of the sampled signals and accumulates them in the register 12a. In this manner, the set of samples Da is accumulated in the register 12a. The sampling part 12 outputs to the arithmetic processing section 2, for each predetermined period of time, a set of samples Da detected within the predetermined period of time and accumulated in the register 12a, in accordance with an instruction from the arithmetic processing section 2. Those samples having been subjected to the analog-to-digital conversion by the amplifier 11a (the outputs of the AE sensors 10a, 10b) (hereinafter, also referred to as "AE data") are outputted from the register 12a to the arithmetic processing section 2 in an electrical unit consisting of a predetermined number of, such as 102400, signals of the AE sensors 10a, 10b. Therefore, AE data is outputted to the arithmetic processing section 2 about every 0.1 seconds (102400/1 MHz ≈ about 0.1 seconds). Therefore, the predetermined period of time for the AE data is, in the present embodiment, about 0.1 seconds. Further, those samples having been subjected to the analog-to-digital conversion by the amplifier 11b (the outputs of the accelerometers 10c, 10d) (hereinafter, also referred to as "acceleration data") are outputted from the register 12a to the arithmetic processing section 2 in an electrical unit consisting of a predetermined number of, such as 65536, signals of the accelerometers 10c, 10d. Therefore, acceleration data is outputted to the arithmetic processing section 2 about every 3.3 seconds (65536/20 kHz ≈ about 3.3 seconds). Therefore, the predetermined period of time for the acceleration data is, in the present embodiment, about 3.3 seconds.

In such detection unit 1, a vibration of the rotating machine 5 is detected by the sensors 10 as analog signals and outputted to the amplifiers 11. The detected signals are then amplified by the amplifiers 11 and inputted to the sampling part 12. The detected signals of the rotating machine 5 inputted to the sampling part 12 are sampled and digitized to be then outputted to the arithmetic processing section 2 at a predetermined timing.

The arithmetic processing section 2 is a device for performing frequency analysis on the samples Da sampled and detected by the detection unit 1, and generating image data for displaying in real time frequency analysis results at a time interval in chronological order. The arithmetic processing section 2 includes, for example, a memory 21, an HDD (Hard Disk Drive) 22, a control arithmetic section 23, an abnormality determination section 24, and an image generation section 25. The memory 21 and the HDD 22 serve as examples of a storage section for storing the samples Da outputted from the detection unit 1. The sampling part 12 is connected to each of the memory 21 and the control arithmetic section 23. The memory 21 is connected to the control arithmetic section 23. The control arithmetic section 23 is connected to each of the HDD 22, the abnormality determination section 24, and the image generation section 25. The abnormality determination section 24 is connected to the image generation section 25. The image generation section 25 is connected to each of the display section 3 and the HDD 22. The control arithmetic section 23 supplies an output to each of the abnormality determination section 24 and the image generation section 25. Therefore, an output of the control arithmetic section 23 is separately supplied to the image generation section 25 via the abnormality determination section 24. The image generation section 25 supplies an output to the display section 3. The HDD 22 receives image data from the image generation section 25.

The memory 21 is in the form of a circuit for temporarily storing a set of samples Da outputted from the sampling part 12. The set of samples Da stored in the memory 21 is read by the control arithmetic section 23. The inclusion of the memory 21 allows all the samples Da outputted from the sampling part 12 to be retained. This makes it possible to store all the samples Da in the HDD 22 to allow the frequency analysis part 23a to performs frequency analysis on all the samples Da.

The HDD 22 is a device for storing the samples Da outputted from the detection unit 1. In the present embodiment, a storage processing part 23b described later stores a set of samples Da stored in the memory 21, for example, in the HDD 22. In the present embodiment, the storage processing part 23b starts to store a set of samples Da in the HDD 22 upon receipt of the set of samples Da from the detection unit 1, for example.

The control arithmetic section 23 performs overall control of the detection unit 1, the arithmetic processing section 2, the display section 3 and the input section 4, and various calculations and the like. The control arithmetic section 23 includes, for example, a processor such as CPU (Central Processing Unit), a ROM (Read Only Memory), a RAM (Random Access Memory) in which the memory 21 is functionally configured, and peripheral circuits. The control arithmetic section 23 includes, for example, the frequency analysis part 23a, the storage processing part 23b, and a control part 23c. In the present embodiment, the control arithmetic section 23 executes an abnormality detection program for detecting an abnormality that is stored in the ROM to cause the frequency analysis part 23a, the storage processing part 23b, and the control part 23c to run on the control arithmetic section 23. Because the frequency analysis part 23a runs on the control arithmetic section 23, the control arithmetic section 23 can functionally configure a plurality of frequency analysis parts 23a in parallel to perform a plurality of frequency analyses in parallel. In the present embodiment, the frequency analysis part 23a and the storage processing part 23b are caused to run on the control arithmetic section 23 to start a frequency analysis and stop running on the control arithmetic section 23 to stop the frequency analysis, for example, simultaneously. The frequency analysis part 23a is connected to the memory 21 and the HDD22, and supplies an output to the abnormality detection section 24 and the image generation section 25. The storage processing part 23b is connected to the memory 21 and the HDD 22.

The frequency analysis part 23a performs frequency analysis of samples Da outputted from the sampling part 12. In the present embodiment, the frequency analysis part 23a performs frequency analysis of the samples Da using Fast Fourier Transform (FFT) and outputs a frequency characteristic of the samples Da, i.e. amplitude data of each frequency, for example.

In the frequency analysis part 23a, a Fast Fourier Transform is performed on AE data for every 4,096 samples, for example. As mentioned above, the AE data is input to the memory 21 for every 102,400 samples. Therefore, the Fast Fourier Transform of AE data is performed 25 times (102,400/4096=25) within the predetermined period of time (about 0.1 second). The frequency analysis part 23a uses, for example, the average value of 25 Fast Fourier Transform results obtained within the predetermined period, as a result of the Fast Fourier Transform of the predetermined period of time. Fast Fourier Transform of acceleration data is performed for every 65,536 samples, for example. Because, as mentioned above, the acceleration data is inputted to the memory 21 for every 65,536 samples, the Fast Fourier Transform of acceleration data is performed once within the predetermined period of time (about 3.3 seconds). In addition, when a termination instruction input part (input section) 4 receives an instruction to terminate an abnormality detection operation from an operator of the abnormality detection device ED, the frequency analysis part 23a reads all sets of samples Da of the previous times that are stored in the HDD and performs frequency analysis thereon and outputs frequency analysis results to the image generation section 25.

The storage processing part 23b stores samples Da read from the memory 21 in the HDD 22. The control part 23c performs overall control of the arithmetic processing section 2. Further, the control part 23c outputs to the sampling part 12 an instruction to output a set of samples Da. In the present embodiment, the collective output instruction is outputted from the control part 23c to the sampling part 12 for each predetermined period of time. The control part 23c outputs to the sampling part 12 an instruction to start sampling and A/D conversion.

The abnormality determination section 24 uses a result of frequency analysis performed in the frequency analysis part 23a to determine the presence/absence of an abnormality in, for example, a rotor of the rotating machine 5. The abnormality determination section 24 extracts from the frequency analysis result a characteristic amount such as the maximum value, the average value, or the standard deviation value of amplitude values, or the median value or the standard deviation value of frequencies, and compares the characteristic amount with a threshold value determined based on the previous abnormality data, experimental results, simulation results or the like, to determine whether the characteristic amount satisfies a predetermined determination condition, thereby determining the presence/absence of an abnormality in the rotor or the like. When the rotating machine 5 is in the form of a compressor, the abnormality determination section 24 outputs to the image generation section 25 a warning message that there is likelihood of contact between two rotors, for example, as an abnormality determination result.

Figure 2:
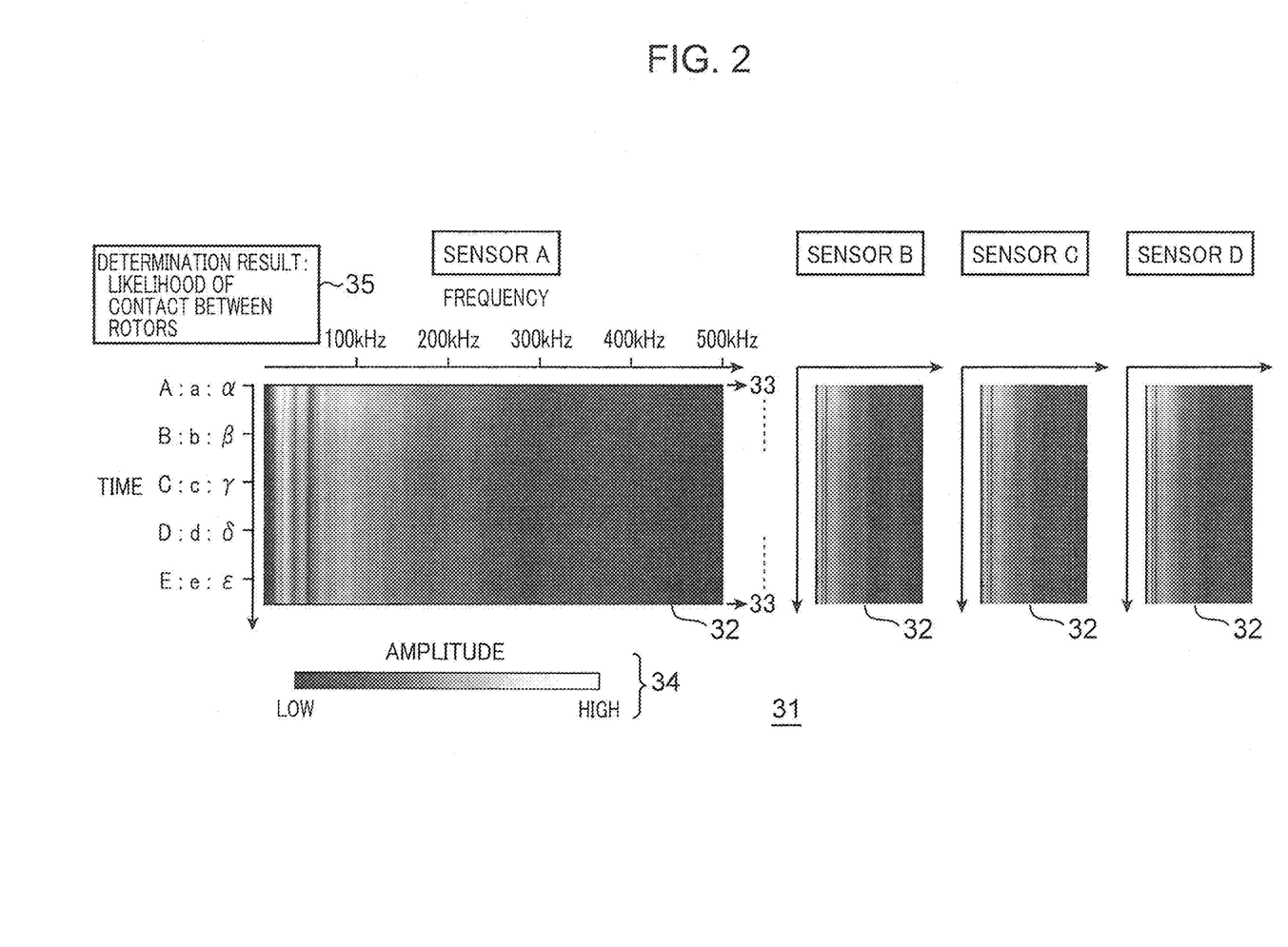
FIG. 2 is an example of a display screen displayed on a display section according to the embodiment.

The image generation section 25 generates image data to be displayed on the display section 3. The image generation section 25 generates, for example, image data for displaying in real time frequency analysis results in chronological order. The image data (hereinafter, also referred to as "three dimensional image data) is, for example, displayed in such a manner that a frequency analysis result is displayed in two dimensions including a frequency axis and an amplitude axis, and frequency analysis results having the most recent frequency analysis result displayed in two dimensions are displayed in real time at a time interval in three dimensions additionally including a chronological order. FIG. 2 shows an example of a display screen 31 on the display section 3. The display screen 31 includes a partial image 32 (image of three dimensional image data) of each sensor (in FIG. 2, each of sensors A to D corresponding to the AE sensors 10a, 10b and the accelerometers 10c, 10d, respectively) in which a frequency analysis result of the current time (in FIG. 2, the time E:e:ε) and frequency analysis results of the previous times (in FIG. 2, the times A:a:α to E:e:ε) are displayed in real time in three dimensions in chronological order. The display screen 31 includes a result display space 35 disposed at a predetermined position for displaying a determination result (such as a warning message), and an explanatory image 34 described later. The partial image 32 displays frequency analysis results with the vertical axis representing time (time axis) and the horizontal axis representing frequency. For the purpose of explanation, FIG. 2 shows the partial image of the sensor A bigger than the partial images of the sensors B to D. The partial image 32 of each sensor is, for example, in the form of a planar image including strip-shaped images 33 arranged in chronological order, each strip-shaped image 33 being displayed in two dimensions including the frequency axis and the amplitude axis. In the case of FIG. 2, the oldest amplitude data (two-dimensional strip-shaped image 33) is deleted from the partial image 33, and the remaining strip-shaped images 33 of the more recent times are scrolled by the amount of the deleted strip-shaped image 32 to allow a new strip-shaped image 33 to be additionally displayed at the bottom under the strip-shaped image 32 of the current time.

In the present embodiment, the amplitude data of each frequency is represented by the shade of monotone of a pixel disposed corresponding to the position of each frequency, for example. The strip-shaped image 33 is displayed in two dimensions in the form of a strip of shades extending along the frequency axis, the strip consisting of a plurality of pixels that are shaded dark to light as the amplitude increases, for example. In FIG. 2, the relationship between the amplitude data and the shades is shown by the explanatory image 34 displayed at a predetermined position in the display screen 31.

The strip-shaped image 33 displayed in two dimensions consists of, for example, 2,048 pixels arranged along the frequency axis. In other words, the strip-shaped image 33 displays the amplitude values of 2,048 frequencies. When a frequency analysis result for frequencies exceeding 2,048 in number is outputted from the frequency analysis part 23a, a specific extraction processing is performed to select 2,048 frequencies to generate a partial image 33. For example, when a frequency analysis result for 4,096 frequencies is outputted, 2,048 frequencies are selected therefrom by comparing the amplitude values of two adjacent frequencies and selecting a frequency of a greater amplitude, for example, and a strip-shaped image 33 consisting of the selected 2,048 pixels arranged along the frequency axis is generated. The above-mentioned method of selecting a frequency of a greater amplitude that indicates a higher possibility of an abnormality allows the abnormality detection device ED to detect an abnormality more suitably.

When the termination instruction input part (input section) 4 receives an instruction to terminate an abnormality detection operation from an operator, the image generation section 25 receives all frequency analysis results (amplitude data) of the previous times obtained by the frequency analysis of the frequency analysis part 23a, and generates three-dimensional image data of the frequency analysis results of the previous times. The three-dimensional image data is transferred to and stored in the HDD 22.

The display section 3 is a device for receiving image data from the image generation section 25 and displays in real time frequency analysis results of the frequency analysis part 23a in chronological order. The input section 4 is in the form of an input device such as a mouse, a key board, or the like that is used to input information to the arithmetic processing section 2. The input section 4 includes the termination instruction input part 4a for receiving from an operator an instruction to terminate an abnormality detection operation after the start of the abnormality detection operation. The termination instruction part 4a may be in the form of a specific key of a keyboard, or a predetermined region (termination instruction input button) displayed on the display section 3 for receiving a termination instruction input.

Figure 3:
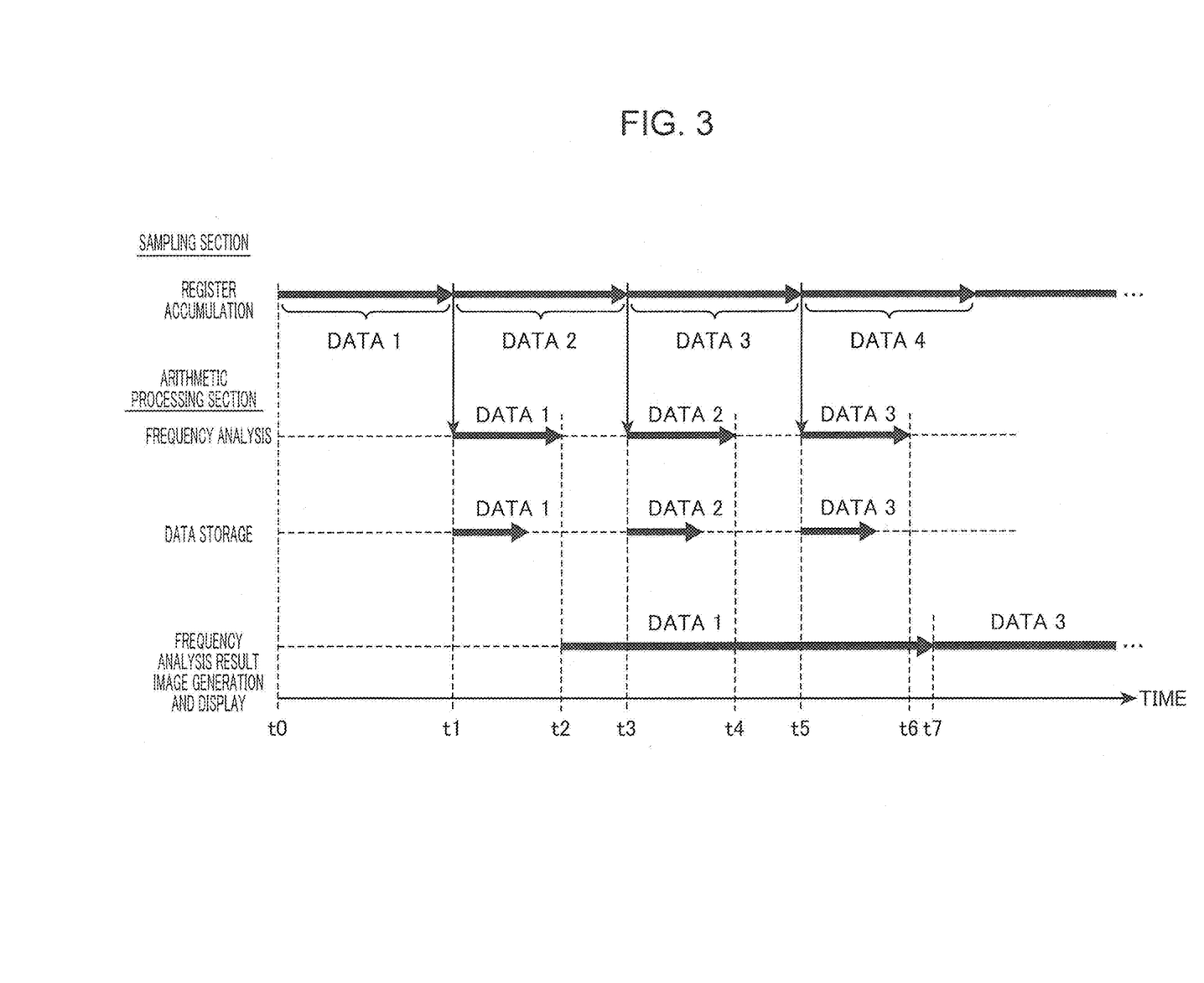
FIG. 3 is a timing chart for explaining the operation of the abnormality detection device for a rotating machine according to the embodiment.

FIG. 3 is a timing chart for explaining the operation of the abnormality detection device for a rotating machine according to the embodiment. FIG. 3 shows a timing chart of each data in the abnormality detection device ED. There are arranged, along the vertical axis, the respective timings of the accumulation processing of the register 12a ("register accumulation" in FIG. 3), the frequency analysis processing of the frequency analysis part 23a ("frequency analysis" in FIG. 3), the storage processing of the storage processing part 23b ("data storage" in FIG. 3), and the image generation processing of the image generation section 25 and the display processing of the display section 3 ("frequency analysis result image generation and display" in FIG. 3). The horizontal axis represents time. Data is accumulated in the register 12a for each predetermined period of time. The time t0 is a time at which the control part 23c instructs the sampling part 12 to start sampling and A/D conversion. During the period between the time t0 and the time t1 being a predetermined period of time after the time t0, the sensors 10 (the AE sensors 10a, 10b and the accelerometers 10c, 10d) detect a vibration of the rotating machine 5, and the amplifiers 11 (11a, 11b) amplify signals and then the sampling part 12 performs sampling and A/D conversion of the signals to accumulate samples Da (data 1 in FIG. 3) in the register 12a. A set of a plurality of samples Da (data 1) detected within the predetermined period of time is accumulated in the register 12a at the time t1, and the accumulated set of samples Da (data 1) is outputted from the register 12a to the memory 21 in accordance with an instruction by the control part 23c. In the same manner as described above, during the time period between the time t1 and the time t3 being the predetermined period of time after the time t1, the vibration detection, the sampling, and the A/D conversion are performed in the detection unit 1 to accumulate samples Da (data 2 in FIG. 3) in the register 12a. At the time t3, a set of a plurality of samples Da (data 2) detected within the predetermined period of time is accumulated in the register 12a, and outputted from the register 12a to the memory 21 in accordance with an instruction by the control part 23c. In this manner, a set of a plurality of samples Da detected within the predetermined period of time is accumulated, for each predetermined period of time, in the register 12a and is outputted collectively. Also after the time t3, accumulation of data 3 or the like in the register 12a and output of the data 3 or the like to the memory 21 are performed in the same manner.

On the other hand, after the time t1, the set of samples Da (data 1) outputted from the register 12a starts to be temporarily stored in the memory 21. The frequency analysis part 23a starts to perform frequency analysis on the samples Da (data 1) upon receipt (the time t1) of the samples Da from the register 12a via the memory 21. The storage section (here, the HDD 22) starts to store the data 1 upon receipt (the time t1) of the samples Da from the register 12a via the memory 21 and the storage processing part 23b. In the present embodiment, the frequency analysis and the storing of the set of samples Da in the storage section are completed by the time t2 before the time t3. In other words, the analysis period (from the time t1 to the time t2) from the start to the end of the frequency analysis on the samples Da (data 1) is shorter than the predetermined period of time (from the time t1 to the time t3), and the storage period from the start to the end of the storing of samples Da (data 1) is shorter than the predetermined period (from the time t1 to the time t3). Hardware having such operating capability is used as the arithmetic processing section 2. The analysis period and the storage period are shorter than the predetermined period of time, which allows all of the samples Da collectively outputted from the sampling part 12 to be subjected to frequency analysis and then stored in the storage section. Also at each of the times t3, t5, and so on after the time t1, the frequency analysis part 23a performs frequency analysis on all of a set of samples Da (data 2, data 3 or the like) and the storage processing part 23b stores all of the set of samples Da (data 2, data 3, or the like) in the HDD 22 for each predetermined period of time. It should be noted that the analysis period and the storage period of the data 2, 3, or the like are also shorter than the predetermined period of time.

Because the frequency analysis part 23a finishes the frequency analysis on the samples Da (data 1) at the time t2, the frequency analysis part 23a starts to output a frequency analysis result to the abnormality determination section 24 and the image generation section 25 after the time t2. Accordingly, after the time t2, the abnormality determination section 24 starts determination of an abnormality and the image generation section 25 generates a strip-shaped image 33 of each sensor with respect to the frequency analysis result of the data 1. The image generation section 25 generates data of the display screen 31 including a partial image 32 (image of three-dimensional image data) to be displayed in real time in chronological order and outputs it to the display section 3. When an abnormality determination result is inputted to the image generation section 25 by the abnormality determination section 24, the image generation section 25 also uses the abnormality determination result to generate image data of the display screen 31. Thereafter, the display section 3 displays the display screen 31. It should be noted that in the present embodiment, there may be cases where the time required for the image generation section 25 to generate image data of the display screen 31 is longer than the predetermined period of time, and the frequency analysis on a set of samples is finished to yield a frequency analysis result of the set of samples during the generation of image data of the display screen 31. In such a case, in the present embodiment, the image generation section 25 uses only the latest frequency analysis result to generate image data of the display screen 31. For example, in FIG. 3, the time t7 at which the generation of image data of the display screen 31 using the frequency analysis result of the data 1 finishes is later than the time t4 at which frequency analysis on the data 2 finishes and the time t6 at which frequency analysis on the data 3 finishes. Therefore, a frequency analysis result of the data 2 and a frequency analysis result of the data 3 have been obtained at the time t7. In this case, the image generation section 25 uses only image data (a striped shaped image 33) of the frequency analysis result of the data 3 that is the latest frequency analysis result, to generate image data of the display screen 31. Accordingly, at the time t7, the image generation section 25 starts to generate image data of the display screen 31 using the data 3 without using the frequency analysis result of the data 2, and the display section 3 displays the display screen 31. Also after the time t7, the abnormality determination by the abnormality determination section 24, the generation of image data of the display screen 31 by the image generation section 25, and the display of the display screen 31 by the display section 3 are performed in similar manners.

Figure 4A:
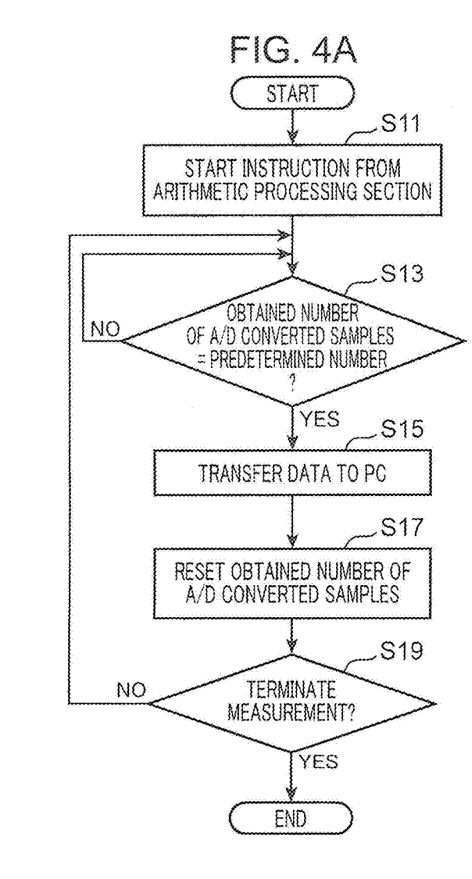
FIG. 4A to 4C are flowcharts of the operation of the abnormality detection device for a rotating machine according to the embodiment.
Figure 4B:
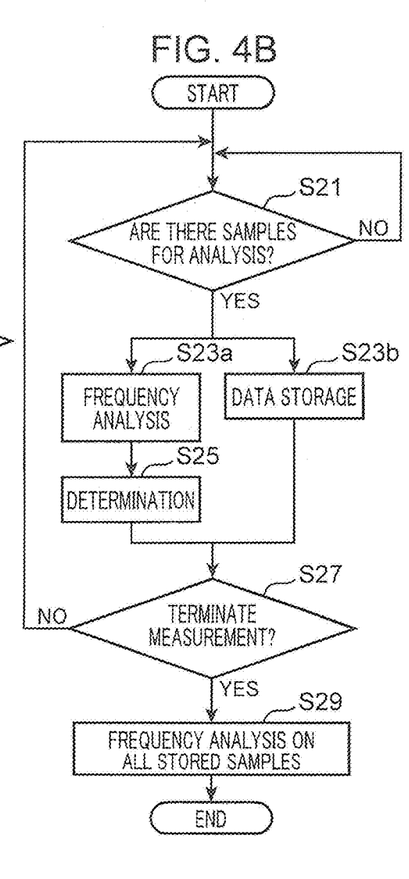
Figure 4C:
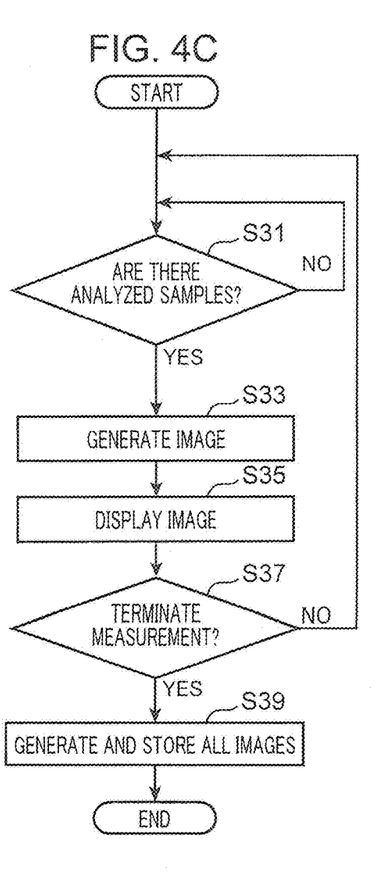

FIGS. 4A to 4C are flowcharts of the operation of the abnormality detection device ED for a rotating machine according to the embodiment. FIG. 4A is a flow chart of operation steps in the sampling part 12, FIG. 4B is a flowchart of operation steps in the frequency analysis part 23a, the storage processing part 23b, and the abnormality determination part 24, and FIG. 4C is a flow chart of operation steps in the image generation section 25 and the display section 3. The operation steps in the flowcharts FIG. 4A to 4C are performed in parallel.

In FIG. 4A, the arithmetic processing section 2 (control part 23c) first outputs to the sampling part 12 an instruction to start sampling and A/D conversion on outputs of the amplifiers 11. The sensors 10 detect a vibration of the rotating machine 5 and the amplifiers 11 amplify signals to be subjected to the sampling and the A/D conversion, so that accumulation of samples Da in the register 12a starts (step S11). From this time, the count of accumulated samples Da having been subjected to the sampling and the A/D conversion (hereinafter, also referred to as "the obtained number of A/D converted samples) in the register 12a starts to increase from zero. Thereafter, the control part 23c determines whether the obtained number of A/D converted samples is equal to the predetermined number (102,400 in the case of AE data, and 65,536 in the case of acceleration data) (step S13). When the count of accumulated samples is less than predetermined number (NO at step S13), the determination at step S13 is repeatedly performed to increase accumulation of samples Da in the register 12a to increase the obtained number of A/D converted samples. When the count of accumulated samples is equal to the predetermined number (YES at step S13), a set of a plurality of samples Da detected within the predetermined period of time is outputted (for each predetermined period of time) from the register 12a to the arithmetic processing section 2 (memory 21) (step S115). Thereafter, the obtained number of A/D converted samples is reset (step S17). Thereafter, the control part 23c determines whether the input section (termination instruction input part) 4 receives an instruction to terminate the abnormality detection operation from an operator (step S19). When no instruction to terminate the abnormality detection operation is inputted by an operator (NO at step S19), the operation returns to step S13 to repeat step S15 at which a set of a plurality of samples Da detected within the predetermined period of time is outputted, and the following steps. When the instruction to terminate the abnormality detection operation is received from an operator (YES at step S19), the abnormality detection device ED performs a predetermined pre-termination processing and then stops the abnormality detection operation.

In FIG. 4B, the control part 23c first determines whether a set of a plurality of samples Da to be subjected to frequency analysis that has been obtained with the predetermined period of time and outputted from the register 12a is stored in the memory 21 (step S21). When it is determined that no set of samples Da is stored (NO at step S21), the determination at step S21 is repeatedly performed. On the other hand, when it is determined that a set of samples Da is stored (YES at step S21), the frequency analysis part 23a performs frequency analysis on samples Da falling within a specific time span (i.e. a time span sufficient to understand a trend in frequency analysis results, such as one second) among the set of samples Da detected within the predetermined period of time (step S23a). In parallel, the storage processing part 23b stores all of the set of samples Da detected within the predetermined period of time in the HDD 22 (step S23b). After the frequency analysis part 23a performs the frequency analysis, the abnormality determination section 24 uses a frequency analysis result to determine the presence/absence of an abnormality in, for example, a rotor in the rotating machine 5 (step S25). Thereafter, the control part 23c determines whether the input section (termination instruction input part) 4 receives from an operator an instruction to terminate the abnormality detection operation (step S27). When no instruction to terminate the abnormality detection operation is inputted by an operator (NO at step S27), the operation steps from step S21 are repeated. When the instruction to terminate the abnormality detection operation is inputted by an operator (YES at step S27), the abnormality detection device ED performs the predetermined pre-termination processing and then stops the abnormality detection operation. In the predetermined pre-termination processing, the frequency analysis part 23a reads all sets of samples Da of the previous times that are stored in the HDD, and performs frequency analysis thereon and outputs frequency analysis results to the image generation section 25 (step S29).

In FIG. 4C, the image generation section 25 first determines whether data of a frequency analysis result is inputted (step S31). When no data of a frequency analysis result is inputted (NO at step S31), the determination at step S31 is repeatedly performed. When data of a frequency analysis result is inputted (YES at step S31), the image generation section 25 generates image data of the display screen 31 (step S33) and outputs the image data to the display section 3, so that the display section 3 displays the image data (step S35). When the image generation section 25 has received an abnormality determination result from the abnormality determination section 24, the image generation section 25 also uses the abnormality determination result to generate image data of the display screen 31. Thereafter, the control part 23*c* determines whether the input section (termination instruction input part) 4 receives from an operator an instruction to terminate the abnormality detection operation (step S37). When no instruction to terminate the abnormality detection operation is inputted by an operator (NO at step S37), the operation steps from step S31 are repeated. When the instruction to terminate the abnormality detection operation is inputted by an operator (YES at step S37), the abnormality detection device ED performs the predetermined pre-termination processing and then stops the abnormality detection operation. In the predetermined pre-termination processing, the image generation section 25 receives frequency analysis results (amplitude data) of the previous times obtained by the frequency analysis of the frequency analysis part 23*a*, and generates three-dimensional image data of the frequency analysis results (amplitude data) of the previous times and transfers the generated data to the HDD 22 (step S39). In this manner, three-dimensional image data of frequency analysis results of the previous times is generated and transferred to the HDD 22 in the predetermined pre-termination processing, which makes it possible to reduce the processing load on the control part 23*c* for storing data in the HDD 22 as compared to the case of storing, each time a frequency analysis result is obtained, the frequency analysis result in the HDD 22 during the frequency analysis.

The abnormality detection device, the abnormality detection program and the abnormality detection method for a rotating machine according to the above-described embodiment display in real time frequency analysis results of samples obtained by sampling a vibration of a rotating machine in chronological order. This makes it possible to represent the chronological change in the operating state of the rotating machine substantially in real time to allow an operator to find a chronological change in the operating state of the rotating machine. Consequently, an abnormality in the rotating machine can be detected promptly.

In the above-described embodiment, the amplifies 11*a*, 11*b* and the sampling part 12 are disposed outside the arithmetic processing section 2, but these components may be incorporated in the arithmetic processing section 2. Further, in the above-described embodiment, display image data of frequency analysis results is outputted from the image generation section 25 to be stored in the HDD 22 after receipt of an instruction to terminate an abnormality detection operation from an operator, but the frequency analysis part 23*a* may store, each time a frequency analysis result is obtained, the frequency analysis result in the HDD 22 (the flow of data shown by the dashed arrow in FIG. 1). In this case, the frequency analysis part 23*a* may start storing a frequency analysis result in the HDD 22 after receipt of samples Da from the detection unit 1 (via the memory 21). Further, in the above-described embodiment, the abnormality determination section 24, the image generation section 25 and the like may also be functionally configured to run on the control arithmetic section 23 by execution of the abnormality detection program stored in the ROM by the control arithmetic section 23.

As an embodiment, there has been described the abnormality detection device ED that integrally includes the detection unit 1, the arithmetic processing section 2, the display section 3, and the input section 4. As another embodiment, an abnormality detection system may be configured that includes a detection unit 1, an arithmetic processing section 2, a display section 3, and an input section 4 in the form of a plurality of mutually communicable devices. Such abnormality detection system includes, for example, an abnormality detection main device comprising the detection unit 1, the arithmetic processing section 2, and the input section 4, and a terminal device communicable with the abnormality detection main device and comprising the display section 3. Alternatively, the abnormality detection system includes, for example, an abnormality detection main device comprising a first arithmetic processing section having the detection unit 1, the memory 21, the HDD 22 and the control arithmetic section 23 and the input section 4, and a terminal device comprising a second arithmetic processing section communicable with the abnormality detection main device and having the abnormality determination section 24 and the image generation section 25 and the display section 3. Alternatively, the abnormality detection system includes, for example, an abnormality detection main device comprising a first arithmetic processing section having the detection unit 1, the memory 21, the HDD 22, the control arithmetic section 23 and the abnormality determination section 24 and the input section 4, and a terminal device comprising a second arithmetic processing section communicable with the abnormality detection main device and having the image generation section 25 and the display section 3. Alternatively, the abnormality detection system includes, for example, an abnormality detection main device comprising the detection unit 1, the arithmetic processing section 2, and a first input section for inputting information to the arithmetic processing section 2, and a terminal device comprising a second input section communicable with the abnormality detection main device and having the display section 3 and a termination instruction input part 4*a*. Such an abnormality detection system can also provide advantageous effects similar to those of the above-described abnormality detection device ED.

The present specification discloses techniques having various aspects as described, among which main techniques are summarized below.

An abnormality detection device for a rotating machine according to an aspect comprises: a detection section for sampling a vibration of a rotating machine to be measured at a predetermined sampling frequency, and outputting, for each predetermined period of time, a set of a plurality of samples detected within the predetermined period of time; a storage section for storing the set of samples outputted by the detection section; a frequency analysis section for performing frequency analysis on the set of samples outputted by the detection section; and a display section for displaying in real time frequency analysis results of the frequency analysis section in chronological order.

A method for detecting an abnormality in a rotating machine according to another aspect comprises: a detection step of sampling a vibration of a rotating machine to be measured at a predetermined sampling frequency, and outputting, for each predetermined period of time, a set of plurality of samples detected within the predetermined period of time; a storing step of storing in a storage section the set of samples outputted from the detection device; a frequency analysis step of performing frequency analysis on the set of samples outputted in the detection step; and a display step of displaying in real time, on a display section, frequency analysis results in the frequency analysis step in chronological order.

An abnormality detection system for a rotating machine according to another aspect comprises: a detection section for sampling a vibration of a rotating machine to be measured at a predetermined sampling frequency, and outputting, for each predetermined period of time, a set of a plurality of samples detected within the predetermined period of time; a storage section for storing the set of samples outputted by the detection section; a frequency analysis section for performing frequency analysis on the set of samples outputted by the detection section; and a display section for displaying in real time frequency analysis results of the frequency analysis section in chronological order.

Owing to the above-described configurations, these abnormality detection device, abnormality detection method, and abnormality detection system for a rotating machine display in real time frequency analysis results of samples obtained by sampling a vibration of a rotating machine in chronological order. This makes it possible to represent the chronological change in the operating state of the rotating machine substantially in real time to allow an operator to find a chronological change in the operating state of the rotating machine. Therefore, these abnormality detection device, abnormality detection method, and abnormality detection system for a rotating machine can promptly detect an abnormality in the rotating machine.

According to another aspect, it is preferred that, in the above-described abnormality detection device for a rotating machine, the frequency analysis section perform the frequency analysis on the set of samples using Fast Fourier Transform, and output amplitude data of each frequency.

According to this configuration, the abnormality detection device for a rotating machine uses Fast Fourier Transform, which makes it possible to suitably display in real time a frequency analysis result.

According to another aspect, it is preferred that, in the above-described abnormality detection device for a rotating machine, the display section display a frequency analysis result in two dimensions including a frequency axis and an amplitude axis, and display in real time frequency analysis results at a time interval in three dimensions additionally including a chronological order.

According to this configuration, the abnormality detection device for a rotating machine, when displaying in real time frequency analysis results of sets of samples in chronological order, displays a frequency analysis result in two dimensions including the frequency axis and the amplitude axis and displays the frequency analysis results in three dimensions including the time axis. This allows an operator to visually understand the chronological change in the operating state of a rotating machine.

According to another aspect, it is preferred that, in the above-described abnormality detection device for a rotating machine, the frequency analysis section start the frequency analysis upon receipt of the set of samples from the detection section, and the analysis period from the start to the end of the frequency analysis be shorter than the predetermined period of time.

According to this configuration, the abnormality detection device for a rotating machine can complete the frequency analysis of the received set of samples within the predetermined period of time, the samples having been received at the beginning of the period.

According to another aspect, it is preferred that, in the above-described abnormality detection device for a rotating machine, the storage section start storing of the set of samples and the frequency analysis result upon receipt of the set of samples from the detection section, and the storage period from the start to the end of the storing of the set of samples be shorter than the predetermined period of time.

According to this configuration, the abnormality detection device for a rotating machine can store the set of samples and the frequency analysis result in the storage section upon the receipt thereof. The abnormality detection device for a rotating machine can store all the samples in the storage section within the predetermined period of time, the samples having been received at the beginning of the period.

According to another aspect, it is preferred that the above-described abnormality detection device for a rotating machine further comprise a termination instruction input section for receiving an instruction to terminate an abnormality detecting operation, wherein when the instruction is received by the termination instruction input section, the frequency analysis section reads all sets of samples stored in the storage section to perform frequency analysis on the read sets of samples and store frequency analysis results arranged in chronological order in the storage section.

According to this configuration, the abnormality detection device for a rotating machine causes the storage section to store frequency analysis results arranged in chronological order when stopping the abnormality detection operation. Therefore, as compared to the case of storing a frequency analysis result during the frequency analysis, it is possible to reduce the processing load of the storage in the control section, for example.

According to another aspect, it is preferred that, in the above-described abnormality detection device for a rotating machine, the frequency analysis section run on a processor by execution of a predetermined frequency analysis program, and the frequency analysis section run on the processor to start the frequency analysis and stop running on the processor to stop the frequency analysis.

According to this configuration, the abnormality detection device for a rotating machine can functionally configure a plurality of frequency analysis sections in parallel. The frequency analysis section is configured when necessary, and therefore, the abnormality detection device for a rotating machine only has to control a frequency analysis section that functionally runs on the processor when necessary. This makes it possible to reduce the processing load of the processor and the like as compared to the case of functionally configuring a predetermined number of frequency analysis sections in advance.

A rotating machine according to another aspect includes an abnormality detection device for a rotating machine according to any one of the above-mentioned aspects.

According to this configuration, there is provided a rotating machine including an abnormality detection device for a rotating machine according to any one of the above-mentioned aspects. Such rotating machine can promptly detect an abnormality in the rotating machine.

This application is based on Japanese Patent Application No. 2014-185872 filed in Japan Patent Office on Sep. 12, 2014, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

INDUSTRIAL APPLICABILITY

The present invention can provide an abnormality detection device, an abnormality detection method and an abnormality detection system for a rotating machine, and a rotating machine.

The invention claimed is:

1. An abnormality detection device for a rotating machine, comprising:
    a detection section for sampling a vibration of the rotating machine to be measured at a predetermined sampling frequency, and outputting, for each predetermined period of time, a set of a plurality of samples detected within the predetermined period of time;
    a storage section for storing the set of samples outputted by the detection section;
    a frequency analysis section for performing frequency analysis on the set of samples outputted by the detection section;
    an image generation section for generating image data of a display screen, the display screen displaying in real time a frequency analysis result of the frequency analysis section in chronological order; and
    a display section for displaying the display screen, wherein
    the frequency analysis section starts the frequency analysis upon receipt of the set of samples from the detection section,
    the analysis period from the start to the end of the frequency analysis is shorter than the predetermined period of time, and
    in a case where a time required for the image generation section to generate the image data of the display screen is longer than the predetermined period of time, so that a plurality of frequency analysis results have been obtained when the image generation section starts to generate the image data of the display screen, the image generation section generates the image data of the display screen using only the latest frequency analysis result.

2. The abnormality detection device for a rotating machine according to claim 1, wherein
    the frequency analysis section performs the frequency analysis on the set of samples using Fast Fourier Transform, and outputs amplitude data of each frequency.

3. The abnormality detection device for a rotating machine according to claim 2, wherein
    the display section displays a frequency analysis result in two dimensions including a frequency axis and an amplitude axis, and displays in real time frequency analysis results at a time interval in three dimensions additionally including a chronological order.

4. The abnormality detection device for a rotating machine according to claim 1, wherein
    the storage section starts storing of the set of samples and the frequency analysis result upon receipt of the set of samples from the detection section, and
    the storage period from the start to the end of the storing of the set of samples is shorter than the predetermined period of time.

5. The abnormality detection device for a rotating machine according to claim 1, further comprising:
    a termination instruction input section for receiving an instruction to terminate an abnormality detecting operation, wherein
    when the instruction is received by the termination instruction input section, the frequency analysis section reads all sets of samples stored in the storage section to perform frequency analysis on the read sets of samples and store frequency analysis results arranged in chronological order in the storage section.

6. The abnormality detection device for a rotating machine according to claim 4, wherein
    the frequency analysis section runs on a processor by execution of a predetermined frequency analysis program, and
    the frequency analysis section runs on the processor to start the frequency analysis and stops running on the processor to stop the frequency analysis.

7. A rotating machine, comprising an abnormality detection device for a rotating machine according to claim 1.

8. The abnormality detection device for a rotating machine according to claim 5, wherein
    the frequency analysis section runs on a processor by execution of a predetermined frequency analysis program, and
    the frequency analysis section runs on the processor to start the frequency analysis and stops running on the processor to stop the frequency analysis.

9. A method for detecting an abnormality in a rotating machine, comprising:
    a detection step of sampling a vibration of the rotating machine to be measured at a predetermined sampling frequency, and outputting, for each predetermined period of time, a set of a plurality of samples detected within the predetermined period of time;
    a storing step of storing in a storage section the set of samples outputted in the detection step;
    a frequency analysis step of performing frequency analysis on the set of samples outputted in the detection step; and
    an image generation step of generating image data of a display screen, the display screen displaying in real time, on a display section, a frequency analysis result in the frequency analysis step in chronological order, wherein
    in the frequency analysis step, the frequency analysis is started upon receipt of the set of samples from the detection step,
    the analysis period from the start to the end of the frequency analysis is shorter than the predetermined period of time, and
    in a case where a time required for the image generation step to generate the image data of the display screen is longer than the predetermined period of time so that a plurality of frequency analysis results have been obtained when the image generation step starts to generate the image data of the display screen, the image generation step generates the image data of the display screen using only the latest frequency analysis result.

10. An abnormality detection system for a rotating machine, comprising:
    a detection section for sampling a vibration of the rotating machine to be measured at a predetermined sampling frequency, and outputting, for each predetermined period of time, a set of a plurality of samples detected within the predetermined period of time;
    a storage section for storing the set of samples outputted by the detection section;
    a frequency analysis section for performing frequency analysis on the set of samples outputted by the detection section;
    an image generation section for generating image data of a display screen, the display screen displaying in real time a frequency analysis result of the frequency analysis section in chronological order; and
    a display section for displaying the display screen, wherein the frequency analysis section starts the frequency analysis upon receipt of the set of samples from the detection section, the analysis period from the start to the end of the frequency analysis is shorter than the predetermined period of time, and in a case where a time required for the image generation section to generate the image data of the display screen is longer than the predetermined period of time so that a plurality of frequency analysis results have been obtained when the image generation section starts to generate the image data of the display screen, the image generation section generates the image data of the display screen using only the latest frequency analysis result.

* * * * *